US009277875B2

(12) United States Patent
Kleinberg et al.

(10) Patent No.: US 9,277,875 B2
(45) Date of Patent: Mar. 8, 2016

(54) DEVICE FOR THE DETECTION OF NON-CAVITATED EARLY DENTAL CARIES LESIONS

(75) Inventors: Israel Kleinberg, Smithtown, NY (US); Fred Confessore, St. James, NY (US); Robi Chatterjee, South Setauket, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 306 days.

(21) Appl. No.: 12/940,589

(22) Filed: Nov. 5, 2010

(65) Prior Publication Data

US 2011/0111361 A1    May 12, 2011

Related U.S. Application Data

(60) Provisional application No. 61/259,012, filed on Nov. 6, 2009.

(51) Int. Cl.
*A61C 3/00* (2006.01)
*A61B 5/053* (2006.01)

(52) U.S. Cl.
CPC .................................... *A61B 5/0534* (2013.01)

(58) Field of Classification Search
CPC ................ A61B 5/053; A61B 5/0534; A61B 2017/00026
USPC ...................... 433/29, 215, 32; 600/547, 554; 33/513–514
See application file for complete search history.

(56) References Cited

U.S. PATENT DOCUMENTS

| | | | | |
|---|---|---|---|---|
| 2,949,107 | A | * | 8/1960 | Ziegler ............................. 433/32 |
| 3,128,759 | A | * | 4/1964 | Bellis ............................... 433/32 |
| 4,197,641 | A | * | 4/1980 | Paulke et al. .................... 433/32 |
| 4,215,698 | A | * | 8/1980 | Nuwayser ...................... 600/547 |
| 4,537,573 | A | | 8/1985 | Sunada |
| 4,552,531 | A | * | 11/1985 | Martin .......................... 433/147 |
| 4,832,599 | A | * | 5/1989 | Kung .............................. 433/32 |

(Continued)

FOREIGN PATENT DOCUMENTS

| | | |
|---|---|---|
| JP | 59-24017 | 2/1984 |
| JP | 3-9715 | 1/1991 |

(Continued)

OTHER PUBLICATIONS

International Search Report dated Jul. 29, 2011 which issued in PCT Application No. PCT/US2010/055660.

(Continued)

*Primary Examiner* — Rene Towa
(74) *Attorney, Agent, or Firm* — Fish & Richardson P.C.

(57) ABSTRACT

The invention provides a device for detecting non-cavitated caries lesions, including a measuring electrode having an electrically conductive tip. The tip is dimensionally configured to fit within a fissure and provide electrical contact with a patient's tooth. A reference electrode is also included, the reference electrode being configured for electrical contact with the patient's body. A measuring means is also provided for determining electrical conductance between the measuring electrode and the reference electrode, wherein the device is further configured to receive a current source for providing electrical current between the measuring electrode and the reference electrode.

29 Claims, 12 Drawing Sheets

(56) References Cited

U.S. PATENT DOCUMENTS

| | | | |
|---|---|---|---|
| 6,424,861 B2 * | 7/2002 | Meredith | 600/547 |
| 6,491,522 B1 | 12/2002 | Jensen | |
| D469,577 S * | 1/2003 | Latone et al. | D28/65 |
| 6,575,747 B1 * | 6/2003 | Riitano et al. | 433/102 |
| 6,845,265 B2 * | 1/2005 | Thacker | 600/547 |
| 2006/0057538 A1 | 3/2006 | Hoeffleur | |
| 2008/0097712 A1 * | 4/2008 | Bruce et al. | 702/77 |
| 2008/0280248 A1 * | 11/2008 | Pitts et al. | 433/32 |

FOREIGN PATENT DOCUMENTS

| | | |
|---|---|---|
| JP | 2003-504100 | 2/2003 |
| WO | WO 01/03544 | 1/2001 |

OTHER PUBLICATIONS

Ie Y.L., Verdonschot E. H., Schaeken, M. J.M.and vant Hof M.A. Electrical conductance of fissure enamel in recently erupted molar teeth as related to caries status. Caries Res. 29: 94-99, 1995.

Longbottom C and Huysmans M.C.D.N.J.M. Electrical measurements for use in caries clinical trials. J. Dent. Res. 83 (Spec. Issue C) C76-C79, 2004).

Pashley D.H. Theory of dentin sensitivity. J. Clin. Dent. 5:65-67, 1994.

Weerheijm KL, van Amerongen WE, and Eggink CO. The clinical diagnosis of occlusal caries: A problem. J. Dent. Child. 56, 196-200, 1989.

Verdonschot E.H., Wenzel A., Truin G.J. and Konig K.G. Performance of electrical resistance measurements adjunct to visual inspection in the early diagnosis of occlusal caries. J. Dent. 21: 332-337, 1993.

Hudson P. and Kutsch V.K. Microdentistry: Current pit and fissure caries management. Compendium 22: 469-483, 2001.

Lussi A., Firestone A., Schoenberg V., Hotz P., and Stich H. In vivo diagnosis of fissure caries using a new electrical resistance monitor. Caries Res. 29: 81-87, 1995.

Williams, D.L., Tsamtsouris A., and White, G.E Electrical resistance correlation with tactile examination on occlusal surfaces. J. Dent. Res. 57: 31-35, 1978.

Pincus, P. A new method of examination of molar tooth grooves for the presence of dental caries. J. Physiol 113: 13-14, 1951.

Mumford, J.M. Relationship between the electrical resistance of human teeth and the presence and extent of dental caries. Brit. Dent. J. 100, 239-244, 1956.

Mayuzumi, Y, Suzuki, K and Sunada, J. A method of diagnosing incipient caries in pits and fissures by measuring electrical resistance. J. Dent. Res. 43, 941, 1964.

Takeuchi, M., Kizu, T., Shimizu, T., Eto, M. and Amano, F. Sealing of the pit and fissure with resin adhesive. II. Results of nine months' field work, an investigation of electrical conductivity of teeth. Bull Tokyo Dent Coll 7, 60-71, 1966.

White G.E., Tsamtsouris A., and Williams D.L. A longitudinal study of electronic detection of occlusal caries. J. Pedod. 5, 91-101, 1981.

Pitts N.B. Clinical diagnosis of dental caries: a European perspective J. Dent. Educ. 65: 972-978, 2001.

Ricketts, D.N.J. Kidd, E.A.M., and Wilson, R.F. A re-evaluation of electrical resistance measurements for the diagnosis of occlusal caries. Brit. Dent. J. 178: 11-17, 1995.

Brannstrom, M; Linden L.A. And Aström A. The hydrōdynamics of the dental tubule and of pulp fluid. Caries Res. 1:310-312, 1967.

Brännström M. Sensitivity of dentine. Oral Surg. Oral Med Oral Pathol 21:517-526, 1966.

Jenkins, G.N. et al., "The Physiology and Biochemistry of the Mouth," Blackwell Scientific Publications, Fourth Edition, Oxford, pp. 60-69 (1978).

Atkinson, H.F. et al., "An Investigation into the Permeability of Human Deciduous Enamel," British Dental J., 89:142-145 (1949).

Office Action issued in Japanese Application No. 2012-537234, dated Jan. 9, 2015, 7 pages (with English Translation).

Atkinson and Mathews, "An Investigation Into the Permeability of Human Deciduous Enamel", British Dental Journal, 86(6):142-145 (Mar. 18, 1949).

Holt et al., "Studies in Calcification. I. The Solubility Product of Secondary and Tertiary Calcium Phosphate Under Various Conditions", J. Biol. Chem., 64(3): 509-565 (Apr. 22, 1925).

Weatherell et al., "Density Patterns in Enamel", Caries Res. 1:42-51 (1967).

Textbook of Cariology, 2d ed., pp. 114-115 and p. 369, (1999) (6 pages).

* cited by examiner

DEVICE FOR THE DETECTION OF NON-CAVITATED EARLY DENTAL CARIES LESIONS

FIELD OF THE INVENTION

The present invention relates generally to detection of dental caries lesions. More particularly, the present invention relates to electrical devices and methods for detecting non-cavitated early dental caries lesions.

BACKGROUND OF THE INVENTION

Dental caries is a disease that frequently occurs soon after teeth erupt into the oral cavity, an environment that is generally hostile to the teeth of most individuals. Sites particularly prone to caries development are the occlusal surfaces of the posterior teeth. This is largely because these surfaces possess a morphology (i.e. pits, fissures and fossae) that favors retention of both fermentable carbohydrate and bacterial biofilms. These two entities are primary elements in dental caries causation. Combined, they result in the production of the acid that leads to tooth demineralization and the initiation and development of dental caries lesions. More tooth decay occurs in occlusal locations and to lesser degree in interproximal dentition sites (where teeth are in contact with one another) than elsewhere in the human dentition. This is because bacteria and fermentable carbohydrate collect more easily there, and are protected from the caries inhibiting effects of saliva, than occurs in other more salivary accessible dentition locations.

Dental caries begins as a demineralization process which leads to the development of pores and tunnels through the protective, non-electrically conductive enamel (Longbottom, C. and Huysmans, M.C.D.N.J.M. Electric measurements for use in caries clinical trials. Caries Res. 29, 94-99, 1995. Longbottom C and Huysmans M.C.D.N.J.M. Electrical measurements for use in caries clinical trials. J. Dent. Res. 83 (Spec. Issue C) C76-C79, 2004). Continued demineralization eventually results in enamel breaching. Once the enamel is breached, caries advances and spreads rapidly through the underlying dentine, a tissue much less mineralized than enamel. Such spreading is made easy because dentine is traversed by numerous tubules. Many, if not most of these dentinal tubules, especially in younger teeth, reach all the way to the dental pulp (Pashley D. H. Theory of dentin sensitivity. J. Clin. Dent. 5:65-67, 1994).

Non-cavitated caries lesions, particularly in the pits, fissures and fossae of the posterior teeth are difficult to detect and assess in humans. Teeth mainly involved include the first and second primary molars and the premolars and molars of the permanent dentition. These teeth and interproximal dentition sites are where the majority of dental cavities occur.

Presently, detection of caries development is mostly done by a dentist or other dental care provider with a simple, pick-like device, generally referred to as a dental explorer. Such detection is performed by visual examination for indications of mineral loss, and is done with or without x-rays. None of these tools is suitable for detection of a high percentage of non-cavitated occlusal caries lesions even when there is caries penetration into the dentine. Many of these early developing caries lesions are not cavitated, but do involve extensive tunneling through the enamel and such tunneling may not be detectable. Such caries development is frequently hard to discover until destruction of tooth substance becomes more substantial and the dentine becomes progressively more and more involved. As a consequence of the difficulty of their discovery, these lesions are commonly referred to as hidden dental caries (Weerheijm K L, van Amerongen W E, and Eggink C O. The clinical diagnosis of occlusal caries: A problem. J. Dent. Child. 56, 196-200, 1989). Their early discovery is often missed or involves much uncertainty. Not surprisingly, there is opportunity for pulpal damage to occur and for teeth to be lost unnecessarily (Verdonschot E. H., Wenzel A., Truin G. J. and Konig K. G. Performance of electrical resistance measurements adjunct to visual inspection in the early diagnosis of occlusal caries. J. Dent. 21: 332-337, 1993). Ironically, the anti-caries agent, fluoride, can be detrimental to early detection, because it favors less cavitation (Hudson P. and Kutsch V. K. Microdentistry: Current pit and fissure caries management. Compendium 22: 469-483, 2001). This is because fluoride reduces the solubility of the enamel covering the dentine, thereby enabling the enamel to remain largely intact while underlying dentine continues to be demineralized (Lussi A., Firestone A., Schoenberg V., Hotz P., and Stich H. In vivo diagnosis of fissure caries using a new electrical resistance monitor. Caries Res. 29: 81-87, 1995). For these reasons, it has become very important that caries lesions be detected as early and as easily as possible.

Because the enamel of freshly erupted teeth commonly exhibit a certain degree of porosity, such teeth are more prone to dental caries development than if they had been exposed in the mouth for an extended period under non-cavity producing and mineralizing conditions. Such improvement is called maturation and occurs because many of these exposed teeth acquire calcium and phosphate ions from saliva along with various proteinaceous accretions. These changes involve increased enamel mineralization, reduced enamel permeability and greater caries resistance. This is helped by fluoride if applied or taken up naturally during the tooth maturation process (Ie Y. L., Verdonschot E. H., Schaeken, M. J. M. and vant H of M. A. Electrical conductance of fissure enamel in recently erupted molar teeth as related to caries status. Caries Res. 29: 94-99, 1995). In contrast, in a caries-prone mouth where a demineralization environment is present, an opposite result occurs more readily, i.e. development of increased porosity and cavitation.

Several approaches have been unsuccessfully used to detect dental caries in its early stages. One of these involves testing for a tooth's ability to conduct electrical current even when there is no visible tooth mineral loss from the enamel and no cavitation can be seen. Electrical resistance is associated with the presence of intact, non-demineralized enamel; but, as a caries lesion develops and enamel mineral is progressively lost, fluid can seep therein and electrical resistance of the enamel correspondingly and progressively decreases (Williams, D. L., Tsamtsouris A., and White, G. E. Electrical resistance correlation with tactile examination on occlusal surfaces. J. Dent. Res. 57: 31-35, 1978, Longbottom C and Huysmans M.C.D.N.J.M. Electrical measurements for use in caries clinical trials. J. Dent. Res. 83 (Spec. Issue C) C76-C79, 2004).

Breaching of enamel occurs more easily in occlusal pit and fissure sites. As noted above, these dentition locations are where continual presence of acidogenic bacteria and fermentable carbohydrate can undergo significant and continual interaction. This favors prolonged generation of acid and in turn, prolonged and extensive tooth demineralization. As this happens, a point is reached where the enamel is sufficiently demineralized and porous that saliva penetrates therethrough and because of the ions that saliva contains, flow of electrical current can take place as a result. The more extensive the demineralization, the more readily these events occur and the easier it is to detect caries lesion development.

Earlier investigators measured electrical resistance or conductivity with direct current devices to determine if a tooth had lost mineral and had become carious (Pincus, P. A new method of examination of molar tooth grooves for the presence of dental caries. J. Physiol 113: 13-14, 1951. Mumford, J. M. Relationship between the electrical resistance of human teeth and the presence and extent of dental caries. Brit. Dent. J. 100, 239-244, 1956. Mayuzumi, Y, Suzuki, K and Sunada, J. A method of diagnosing incipient caries in pits and fissures by measuring electrical resistance. J. Dent. Res. 43, 431, 1964. Takeuchi, M., Kizu, T., Shimizu, T., Eto, M. and Amano, F. Sealing of the pit and fissure with resin adhesive. II. Results of nine months' field work, an investigation of electrical conductivity of teeth. Bull Tokyo Dent Coll 7, 60-71, 1966. Williams, D. L., Tsamtsouris A., and White, G. E. Electrical resistance correlation with tactile examination on occlusal surfaces. J. Dent. Res. 57: 31-35, 1978). Others subsequently used alternating current and measured impedance to do essentially the same thing White G. E., Tsamtsouris A., and Williams D. L. A longitudinal study of electronic detection of occlusal caries. J. Pedod. 5, 191-201, 1981. Pitts N. B. Clinical diagnosis of dental caries: a European perspective J. Dent. Educ. 65: 972-978, 2001). In each case, a cavity detecting device was provided, including a measuring probe made of a conducting metal, a direct or alternating current source, a resistance source, an impedance or conductance detector, and a reference electrode suitable for application, generally by attachment to a non-oral soft tissue part of the body. The human body is sufficiently conductive electrically to enable complete electrical continuity via the body between the measuring probe (i.e. the indicator electrode) and a reference electrode usually attached by adhesive means to a body surface such as the ventral surface of the forearm or the back of the neck or by means of a metal hook, the end of which is immersed in the mouth saliva usually by curling around the lower lip.

Tooth enamel is electrically non-conductive unless it is breached by demineralization or fracture. When this occurs, fluid at or entering the breached enamel site enables completion of an electrical circuit that allows current to flow. The electrical current used may be as low as a few micro-amperes ($\mu A$) in magnitude. Hence, it is safe even for use in medically compromised patients. In addition, the procedure is painless.

It has previously been found that special precautions have to be taken while making measurements to ensure electrical continuity without causing any peripheral electrical conductance to saliva or other moisture on the tooth or to saliva or other conductance means elsewhere in the mouth. Such isolation of the measuring electrode from surrounding saliva is an absolute requirement for success. Complete isolation can be achieved by using a rubber dam (Williams, D. L., Tsamtsouris A., and White, G. E. Electrical resistance correlation with tactile examination on occlusal surfaces. J. Dent. Res. 57: 31-35, 1978). However, such use of a dam is cumbersome and is not practical when an extensive mouth examination is required. Instead, most investigators have used a stream of air from an air syringe in an attempt to dry the tooth around but not at the measuring site. To do this simply, consistently and rapidly has been a major problem.

Ricketts et al. used a stream of air surrounding the measuring electrode to isolate the measuring site from surrounding surface electrical conduction (Ricketts, D. N. J. Kidd, E. A. M., and Wilson, R. F. A re-evaluation of electrical resistance measurements for the diagnosis of occlusal caries. Brit. Dent. J. 178: 11-17, 1995). However, the large size of the measuring tips used by these investigators prevented accurate measurements. Further, such large tips, with their drying feature, were not suitably shaped or sized for many of the sites that required more effective probing.

Current methods often yield false and/or variable readings. Current methods also lack the ability to rapidly and consistently detect non-cavitated caries lesions early and accurately. Basically, detection of non-cavitated caries lesions requires electrical linkage between the measuring electrode at the enamel surface measuring site and fluid within the caries lesion. Detection also requires the absence of any electrical conductance immediately around the lesion site. Furthermore, a method of instantly knowing that detection is operating properly is necessary.

SUMMARY OF THE INVENTION

The invention provides a device for detecting non-cavitated caries lesions, including a measuring electrode having an electrically conductive tip. The tip is dimensionally configured to fit within a fissure and provide electrical contact with a patient's tooth without the addition of an external electrical conducting means between measuring tip and tooth. Various fluids have been used in the prior art for this purpose. A reference electrode is also included, the reference electrode being configured for electrical contact with the patient's body. A measuring means is also provided for determining electrical conductance between the measuring electrode and the reference electrode, wherein the device is further configured to receive a current source for providing electrical current between the measuring electrode and the reference electrode.

The invention also provides a method for detecting non-cavitated caries lesions. The method includes the steps of providing a reference electrode for electrically conductive contact with a patient's body, and providing a measuring electrode having an electrically conductive tip, which is dimensionally configured to fit within a fissure and provide electrical contact with a patient's tooth without the addition of electrical conducting means between measuring tip and tooth. The measuring electrode is configured to fit within a fissure and provide electrical contact with a patient's tooth. Electrical current is provided between the measuring electrode and the reference electrode, and electrical conductance between the measuring electrode and the reference electrode is determined.

These and other objectives and advantages of the present invention will be more readily apparent from the following detailed description of the drawings and preferred embodiments.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

DETAILED DESCRIPTION OF THE PREFERRED EMBODIMENTS

Figure 1A:
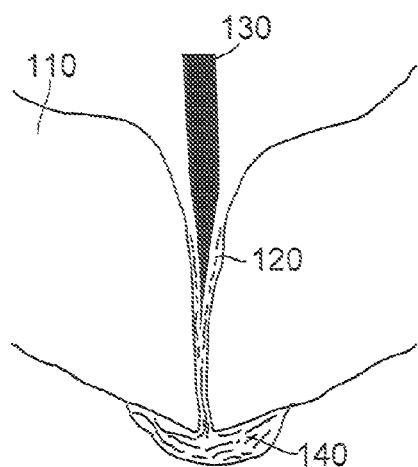
FIG. 1A is a schematic representation of a probe being introduced into a fissure, according to the present invention.

FIG. 1A is a schematic representation of a probe being introduced into a fissure 120. As used herein, the term "fissure" may include any tooth pits, fissures, fossae, or other similar regions or irregularities in the tooth. As indicated in FIG. 1A, early dentinal caries lesions 140 may form and spread out below the enamel 110. These early dentinal caries lesions 140 are very common and are usually incapable of being detected through a traditional visual-tactile inspection or by x-rays. Conventional measuring probes 130 are either too large or not properly tapered to reach sufficiently into the pits and fissures where these lesions are mostly found, as will be described below in more detail (see FIGS. 2C and 2D). The size and shape of the measuring electrode tip 130 is crucial to early caries lesion detection 140 and in the obtaining of consistent and accurate measurements.

Figure 1B:
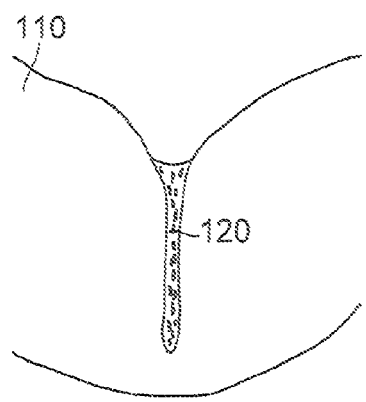
FIG. 1B is a schematic representation of a fissure having a narrow slit.
Figure 1C:
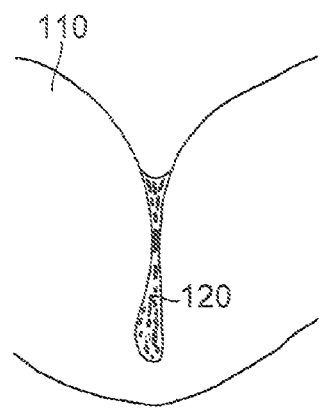
FIG. 1C is a schematic representation of a fissure having the shape of a constricted hourglass.
Figure 1D:
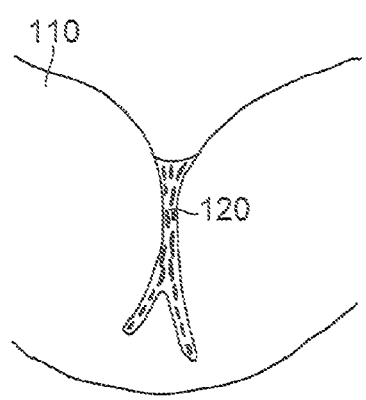
FIG. 1D is a schematic representation of a fissure having an inverted Y-shaped division.

As seen in FIG. 1A, the fissure 120 formed in the enamel 110 may begin as a wide opening at the top of the enamel and become narrower towards the dentin. It will be understood that fissures 120 may also have been formed in the enamel 110 in various shapes. For example, fissures 120 may be wide at the top and gradually narrowing toward the bottom as seen in FIG. 1A. The fissures 120 may also have almost the same width from top to bottom or include extremely narrow slits as seen in FIG. 1B. Fissures 120 may also include inverted Y-shaped divisions (FIG. 1D) or be formed as constricted hourglasses (FIG. 1C). In some embodiments, the width of the fissure 120 ranges from about 0.05 to about 0.3 mm. In at least some embodiments, the width of the fissure 120 ranges from about 0.1 to about 0.2 mm. The length of the fissure 120 may be from about 0.5 mm to about 1.5 mm. The length of the fissure 120 may also be from about 0.75 mm to about 1.25 mm.

Thus, an important distinction between the present invention and the prior art is the difference in size and shape of the measuring electrode tip 130. Thus, the present measuring probe 130 is smaller in diameter and more appropriately tapered so that it can reach more deeply into pits and fissures (and other poorly accessible sites). The dimensions of the probe tip 130 enable contact with fluid present more deeply within the enamel and dentin beneath the enamel (or cementum) at breached sites. Such fluid is almost always present but not in sufficient quantities and close enough to the enamel surface after drying to be reached consistently with the electrodes used in the prior art for making accurate electrical conductance or resistance measurements, and particularly without the need for an external electrical conducting means between measuring tip and tooth.

Figure 2A:
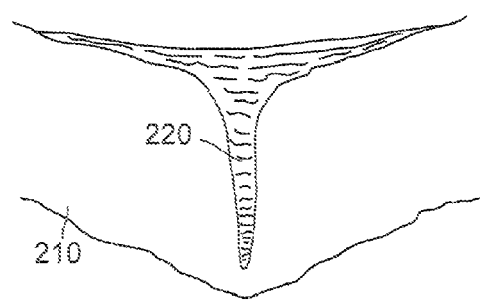
FIG. 2A is a schematic representation of a fissure in enamel before drying.
Figure 2B:
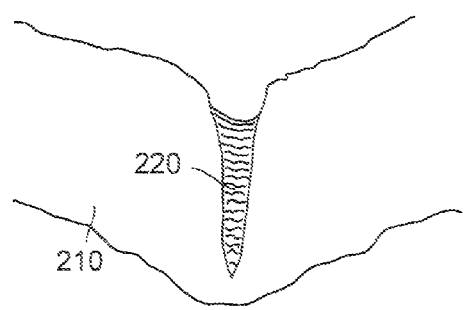
FIG. 2B is a schematic representation of a fissure in enamel after drying.
Figure 2C:
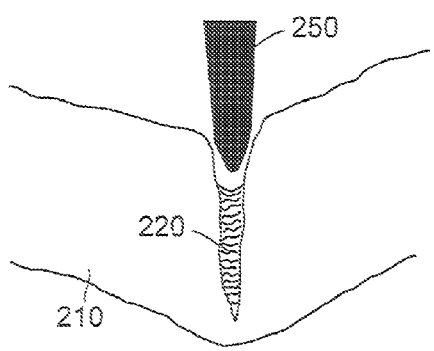
FIG. 2C is a schematic representation of detection via a prior art electrode probe after drying.

Turning to FIGS. 2A-2D, if there is electrical continuity between the tip of the measuring electrode and fluid 220 within an early enamel lesion formed in enamel 210, then there is no need to apply a conducting fluid or medium between electrode and lesion as has been required in the methods put forth in the prior art. However, if the probe tip does not reach fluid 220 after drying the tooth surface with blown air, then the result is an open circuit. Probes 250 that do not penetrate sufficiently, easily result in some air remaining between probe tip 250 and fluid 220 within the lesion as seen in FIG. 2C. This does not happen when probe tips 260 are smaller, and more appropriately shaped and positioned as in FIG. 2D. This is because air is non-conducting and if sufficient air is left after air drying, then there will be no current flow. The result is a zero electrical conductance reading (i.e. a false negative), which is also the reading obtained when there is no caries lesion present (i.e. a true negative). Inadequate surface drying can be a significant problem, because excess surface moisture will yield a reading suggesting lesion presence (i.e. a false positive) when such is not the case.

As noted above, use of a rubber dam to isolate a tooth from its generally wet, oral surroundings will make achievement of the necessary drying conditions certain. By this means, there is no saliva at the measurement site contiguous with saliva or other conducting fluid in the mouth. With rubber dam use, one has complete tooth isolation and can freely employ a conductive means, such as saline or a paste such as toothpaste. These will readily ensure electrical continuity between measuring probe and fluid within the caries lesion (Williams et al, 1978). However, in the absence of a rubber dam a conductive means such as toothpaste may have constituents that cannot be dried and collateral conductance cannot be avoided. However, as pointed out above, use of a rubber dam as a saliva barrier device results in a very slow examination process and hence is not clinically practical, except perhaps in limited caries diagnostic situations.

Previous investigators have dipped the measuring end of the measuring probe into a patient's saliva, or another conducting fluid, paste, or salt solution such as saline just before probe placement followed by air drying (Williams et al, 1978). This has proven difficult to do rapidly and consistently while ensuring probe and caries lesion electrical connection without lateral saliva conductance. From such attempts, it became clear that drying to avoid lateral oral electrical conductance was too difficult to achieve consistently, repetitively and within a short period of time such as a few seconds. It is important to be able to probe each tooth within such a time period in vivo. Otherwise, the procedure (especially if multiple tooth examination is desired) can take too long and becomes impractical.

Lussi et al (1995) like Ricketts et al (1995) above used a shield for drying around the measuring site and measuring tip with some success, while others tried to achieve reproducibility simply by applying a constant flow of air for a fixed period of time. However, the former reduces probe access capability and rapid probing to identify sites of conductance. The latter standardized drying procedure has proven to be less suitable and reliable for clinical investigation or clinical practice than is desirable.

Figure 2D:
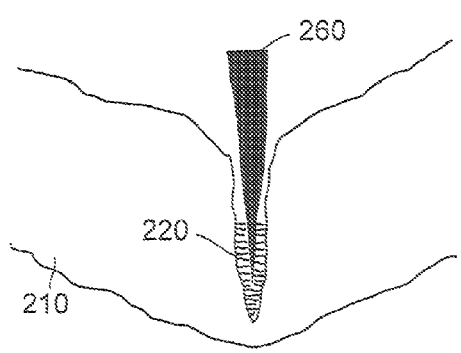
FIG. 2D is a schematic representation of detection via an electrode probe according to the present invention.

In contrast to conventional measuring electrodes, the present invention utilizes electrodes with a shape and dimensions that enable suitable placement and penetration of the measuring probe into pit and fissure sites as seen in FIG. 2D. This method enables the measuring electrode 260 to be placed into a pit or fissure wherein (i) deep lying dentinal fluid is difficult or impossible to displace during air drying and (ii) coronal seepage of pulpal/dentinal fluid (because of hydrostatic and capillary pressures that exist within dentinal tubules; Brannström, 1967), was sufficient to ensure access by a more effective penetrating electrode, even after significant drying of the tooth surface around the measuring site. When breaching occurs, dentinal tubules are exposed and tubules become open to the oral environment. As a consequence, coronal measurement of dentinal fluid conductance, both electrical and hydraulic, can be more readily accomplished (Brannström, et al, 1966 and 1967). Air drying may reduce superficial fluid within a breached site, but coronal seepage from the depths of breached sites can spontaneously make up for such fluid deficiency.

As a protective layer, root cementum behaves like enamel but its breaching differs from enamel in that cementum is thinner and generally more porous and very hard to keep dry.

Figure 3A:
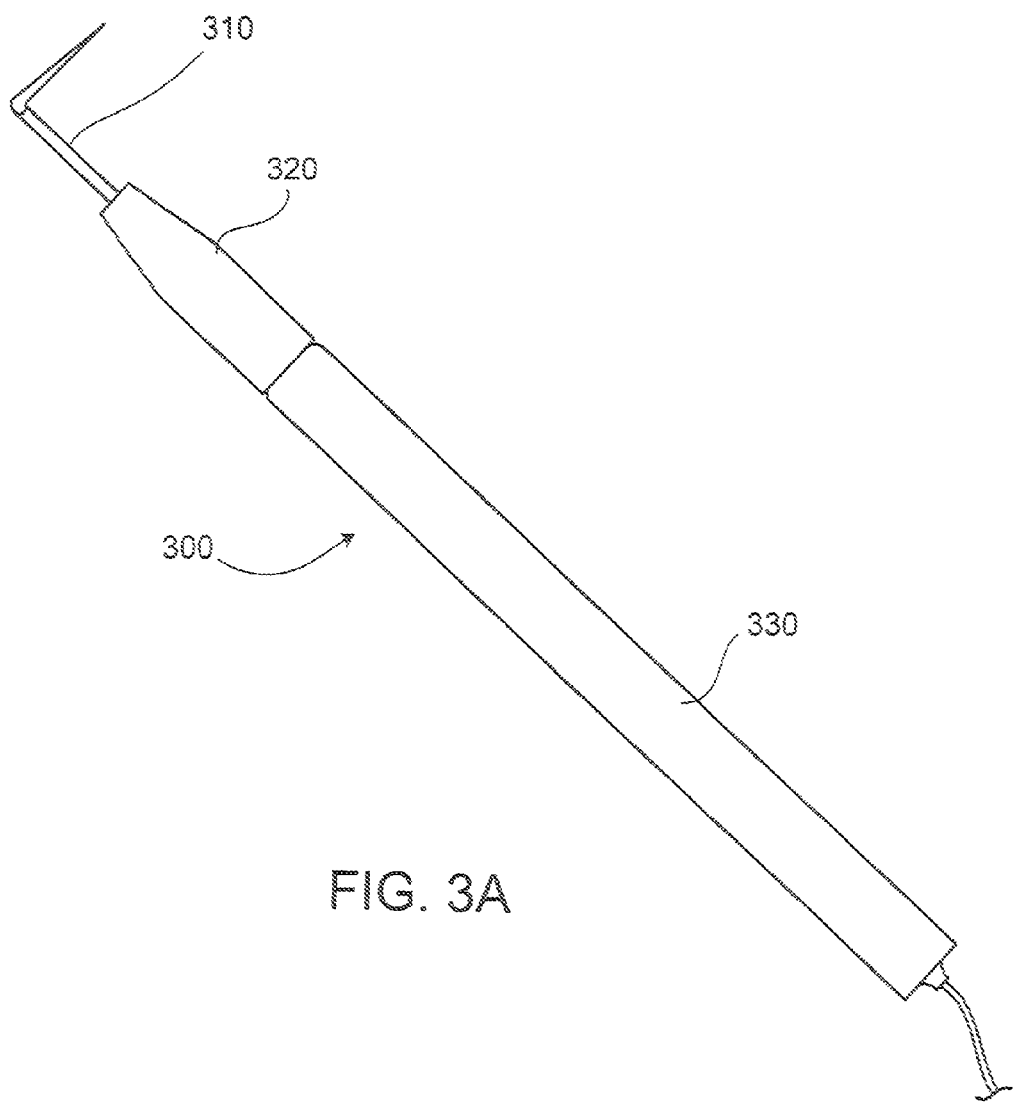
FIG. 3A is a schematic perspective view of a hand-held measuring probe, according to the present invention.
Figure 4A:
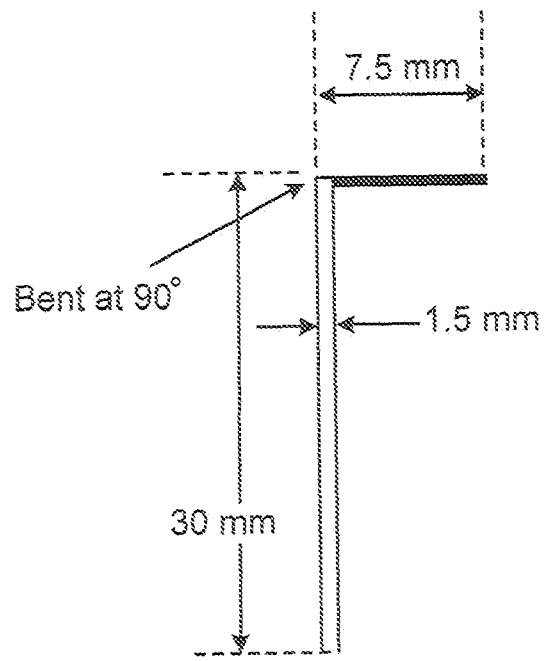
FIG. 4A is a schematic representation of a measuring tip, according to the present invention.
Figure 4B:
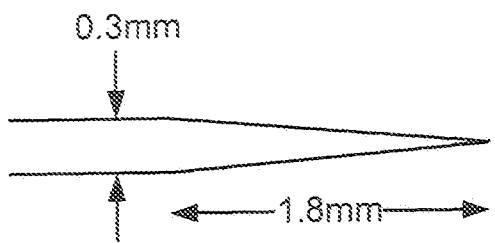
FIG. 4B is a schematic side view of a measuring tip, according to the present invention.

FIG. 3A is a schematic perspective view of a hand-held measuring probe 300. Specifically, a hand-held measuring probe 300 consists of three parts, an electrically insulated handle portion 330, an insulating tightening knurl 320 and an easily replaceable, removable, substantially right angle shaped, measuring probe attachment or probe tip 310 (see FIGS. 3A and 4). The probe tip 310 may be made from a metal such as stainless steel, which is very strong, flexible, and able to withstand the physical manipulation and stresses involved. The measuring probe attachment 310 is preferably right angle shaped to make it easier to line up the probe tip for direct insertion into a tooth site of interest. Other angulations are also possible but are less desirable. The part of the removable measuring tip 310 that is inserted into the tightening knurl 320 may range from 20.0 to 40.0 mm in length. In some embodiments, the part of the removable measuring tip 310 that is inserted into the tightening knurl 320 and/or handle 330 is approximately 30 mm in length. Furthermore, this portion may range from 1.0 to 2.0 mm in diameter. In some embodiments, the portion is 1.5 mm in diameter. The distance from the bend to the tip may range from 6.0 to 9.0 mm. In some embodiments, the distance is 7.5 mm. The diameter after the bend before tapering to a sharply pointed cone may be in the range of 0.2 to 0.4 mm. In some embodiments, the diameter after the bend is 0.3 mm. As seen in FIG. 4A, the tip needs to include a taper to achieve a sharp point. In a suitable embodiment, the taper to the sharp point falls in the range between 5° and 30°. A taper to a sharp point at an angle of 10° is preferable. This results in the length of the taper being 1.8 mm as illustrated in FIG. 4B. In some embodiments, the length of the taper may be between 1.6 and 2.0 mm. The shape and sharp tip enables maximum penetration of the measuring probe into pit and fissure sites to where it is easier to have fluid consistently present as described in FIG. 2. In some embodiments, the tip has a diameter of 0.03 to 0.06 mm with a preference of 0.03 to 0.05 mm.

An easily attached and removable tip that is disposable is highly desirable for ease of use and to ensure no contamination. The probe part may be made from a metal of sufficient strength and flexibility to enable shaping to a fine measuring tip and to be capable of re-use if desired. Orthodontic stainless steel wire that has proven suitable for this purpose has been identified as 304V (Rocky Mountain Orthodontics, Denver, Colo.). It has the chemical formula: Carbon 0.066%, Manganese 1.26%, Phosphorus 0.018%, Sulfur 0.001%, Chromium 18.59%, Nickel 8.80%, Molybdenum 0.15%, Nitrogen 0.025%, Copper 0.25%, Cobalt 0.15%, with Iron making up the balance. This wire material and its probe tips are easy to sterilize with minimal effect on their physical and electrical properties. For commercial reasons, because the probe electrodes are simple and can be made inexpensively, they may be made disposable. If so, attachment to the handle of the measuring electrode can be by a knurl means or by spring tension contact between extension and coiling of the rigid part of the electrode tip 310 which is inserted into the handle 320, where it makes electrical contact.

Figure 3B:
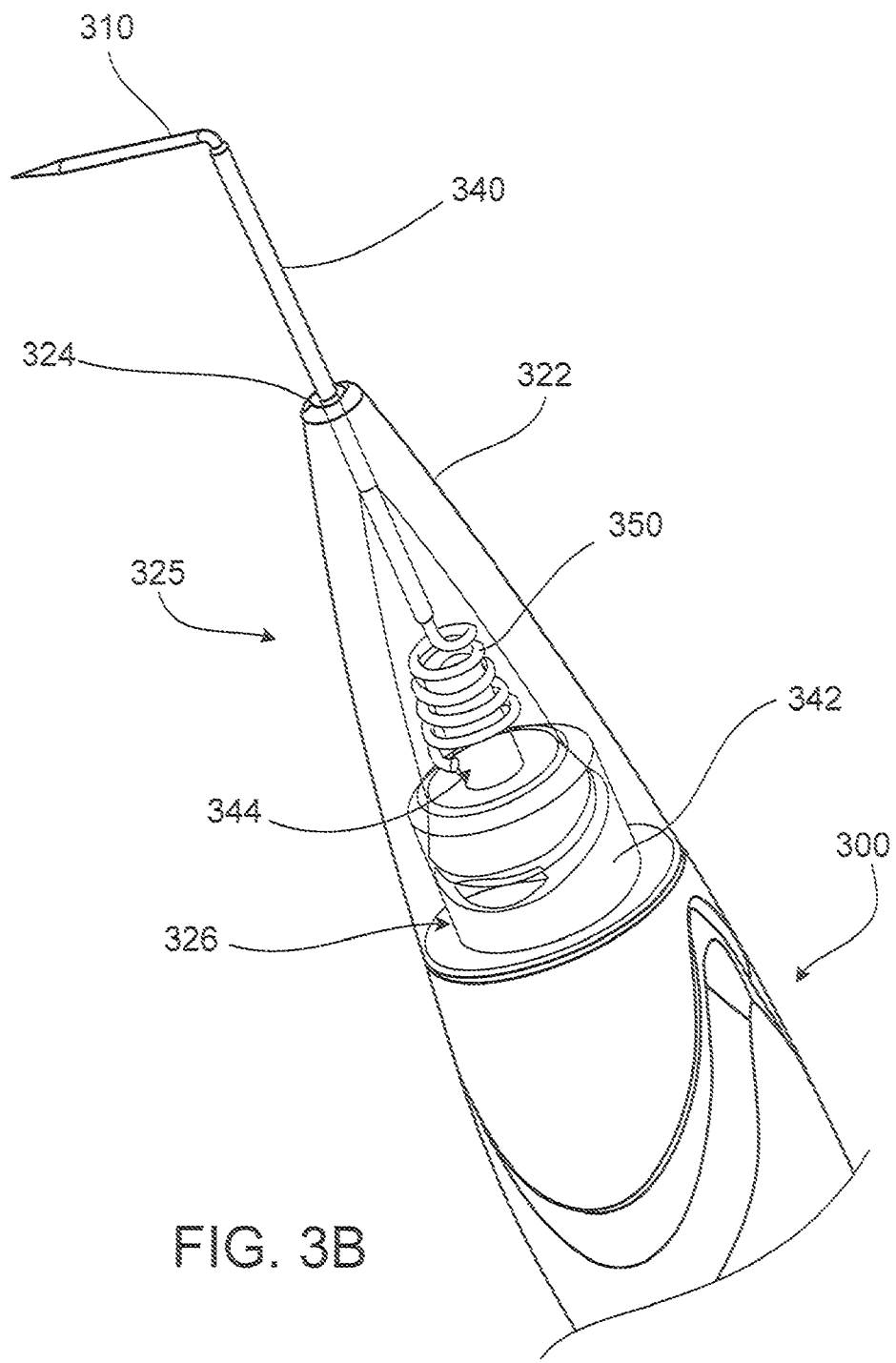
FIG. 3B is a schematic perspective view of a removable measuring tip mounted to the probe of FIG. 3A.

Referring to FIG. 3B, a removable electrode tip 325 is shown mounted on probe 300. Tip 325 includes a tapered tip housing 322 with an opening 324 at the distal end and a snap fit or threaded portion at the proximal end 326. Electrode tip 310, having a co-axial stiffening sheath 340 passes through opening 324 of housing 322 and is secured therein, and terminates in coiled spring section 350.

Probe 300 terminates in an electrode end having a tip anchor 342 with an electrical contact 344 protruding therethrough. In operation, tip 325 is mounted to probe 300 by securing the snap-fit or threaded portion of tip housing 322 to anchor 342. At the same time, coiled spring section 350 is compressed onto and brought into electrical contact with electrical contact 344.

Use of an indicator electrode with the penetrating electrode tip just described, eliminates the need for a fluid applied orally as a conducting means. In prior approaches to measuring conductivity, the electrode dimensions and shape required application of a fluid to ensure electrical contact with dentinal fluid. The present approach simplifies the invention considerably by eliminating this requirement and most importantly, it enables the user of the device to make measurements much more rapidly and accurately than previously possible.

Drying of any saliva on the tooth surface to eliminate surface electrical conductance is usually accomplished with a brief 5 to 10 second blast of dry air from a dental air syringe. This easily dries most occlusal surfaces and the entrances to pits and fissures under measurement but it has little or no effect on the fluid sitting more deeply (and not readily reachable by the blown air) within the pit or fissure lesions being measured. Coating the measuring electrode with a conducting fluid such as saline by dipping the tip into such a fluid has been used to facilitate conductivity with electrodes greater in dimensions than those disclosed herein (Williams et al, 1978). But some air is commonly left in the process and a reading of zero results, whether there is a lesion present or not.

In essence, with conventional electrodes, accessibility is largely limited to pit and fissure entrances as seen in FIG. 2C. Hence, an oral source of electrical conducting fluid, whether it is saliva or an extra-oral occlusal additive, becomes necessary. This makes it hard to achieve reproducibility, especially in the short period of time needed in order for the process to be practical. In contrast, the present invention needs no conductance adjuvant.

Electrical Conductance Measurement

In order to detect caries lesions, electrical conductance may be measured. In some embodiments, a measuring instrument features: (i) a battery powered DC current source that supplies current as needed, (ii) a digital μA meter to measure current, (iii) a digital voltmeter to measure voltage (if desired), (iv) a circuit board that enables several functions that facilitate the taking of rapid, stable and reproducible conductance readings, (v) a reference electrode placed distant from the measuring site so that it does not interfere physically with measurements at dentition sites of interest and (vi) an electrically insulated measuring indicator probe, with a handpiece (e.g. # XHP1, Ellman International, Oceanside, N.Y. 11572) and a replaceable measuring tip.

The 9 volt battery that powers the circuitry of the instant device may produce an unregulated current source limited to an output of 10 μA. It provides an open circuit output of 9 volts and 0 μA. These values correspond to the situation where the probe is not in contact with a tooth site under measurement or is in contact with a tooth site under measurement when the enamel is intact (i.e. with no demineralization). In contrast, if the enamel (or cementum) is breached, as occurs when sufficient caries demineralization has developed and the breach is filled with dentinal or oral fluid, electrical conductance occurs. When the electrical circuit is closed, the current rises to a value greater than zero. This occurs when there is a lesion and the rise in current is proportional to the magnitude of the lesion. Decrease in potential and resistance also occurs, as can be seen from Tables 1 and 2 below. In some embodiments, no external electrical current is applied in order to ensure patient safety.

TABLE 1

Table relating the Ohm's Law variables: conductance (I) to resistance (R), and electrical potential (V) when the battery voltage is 8.61 volts.

| R (OHMS) | V (VOLTS) | I (MICRO AMPS) | R = V/I |
|---|---|---|---|
| Open | 8.61 | 0.00 | 0.0 |
| 22.0M | 8.30 | 0.37 | 22.0M |
| 15.0M | 8.27 | 0.55 | 15.0M |
| 10.0M | 8.24 | 0.81 | 10.1M |
| 6.8M | 8.21 | 1.19 | 6.9M |
| 4.7M | 8.15 | 1.70 | 4.8M |
| 2.7M | 8.04 | 2.87 | 2.8M |
| 1.8M | 7.95 | 4.16 | 1.9M |
| 1.0M | 7.65 | 6.92 | 1.1M |
| 800.0K | 7.55 | 8.30 | 909.0K |
| 600.0K | 6.61 | 9.35 | 706.0K |
| 400.0K | 4.82 | 9.54 | 505.0K |
| 200.0K | 2.93 | 9.72 | 301.0K |
| 100.0K | 1.98 | 9.82 | 201.0K |
| 80.0K | 1.79 | 9.84 | 181.0K |
| 60.0K | 1.59 | 9.86 | 161.0K |
| 40.0K | 1.40 | 9.88 | 141.0K |
| 20.0K | 1.20 | 9.91 | 121.0K |
| 10.0K | 1.10 | 9.92 | 110.0K |
| 8.0K | 1.08 | 9.92 | 108.0K |
| 6.0K | 1.06 | 9.92 | 106.0K |
| 4.0K | 1.04 | 9.92 | 104.0K |
| 2.0K | 1.02 | 9.92 | 102.0K |
| 1.0K | 1.01 | 9.92 | 101.0K |
| 0.0K | 1.00 | 9.92 | 100.0K |

Measurements showing that, as the electrical conductance increases, the voltage and the resistance both decrease. This pattern is reflective of increase in severity of dental caries. The calculated values of circuit resistance closely match the resistance (R) column, $R_1 + R_s$ (100,000 + 1000 Ohms).

TABLE 2

Table relating the Ohm's Law variables: conductance (I) to resistance (R) and electrical potential (V) when the battery voltage is 6.37 volts.

| R (OHMS) | V (VOLTS) | I (MICRO AMPS) | R = V/I |
|---|---|---|---|
| Open | 6.37 | 0.00 | 0.0 |
| 22.0M | 6.34 | 0.28 | 22.6M |
| 15.0M | 6.33 | 0.42 | 15.0M |
| 10.0M | 6.30 | 0.63 | 10.0M |
| 6.8M | 6.28 | 0.91 | 6.9M |
| 4.7M | 6.24 | 1.30 | 4.8M |
| 2.7M | 6.15 | 2.19 | 2.8M |
| 1.8M | 6.06 | 3.18 | 1.9M |
| 1.0M | 5.89 | 5.31 | 1.1M |
| 800.0K | 5.78 | 6.37 | 907.0K |
| 600.0K | 5.62 | 7.95 | 706.0K |
| 400.0K | 4.82 | 9.54 | 505.0K |
| 200.0K | 2.93 | 9.73 | 301.0K |
| 100.0K | 1.98 | 9.83 | 201.0K |
| 80.0K | 1.79 | 9.84 | 181.0K |
| 60.0K | 1.59 | 9.86 | 161.0K |
| 40.0K | 1.40 | 9.87 | 141.0K |
| 20.0K | 1.20 | 9.90 | 121.0K |
| 10.0K | 1.10 | 9.90 | 111.0K |
| 8.0K | 1.08 | 9.91 | 108.0K |
| 6.0K | 1.07 | 9.92 | 107.0K |
| 4.0K | 1.05 | 9.93 | 105.0K |
| 2.0K | 1.03 | 9.93 | 103.0K |
| 1.0K | 1.02 | 9.93 | 102.0K |
| 0.0K | 1.00 | 9.93 | 100.0K |

Measurements showing that when the electrical conductance increases, the voltage and the resistance both decrease. This pattern is reflective of increase in severity of dental caries. The calculated values of circuit resistance closely matches the resistance (R) column, $R_1 + R_s$ (100,000 + 1000 Ohms)

Moreover, completion of the circuit when any reading is made may be linked to a maximum current flow of 10 μA. As seen in Table 3, most early lesion readings are below 4 μA:

TABLE 3

Electrical Conductance and Demineralization Scores of Test Teeth

| Tooth # | Current (μA) | Demineralization score |
|---|---|---|
| 32 | 1.9 | 2 |
| 15 | 3.0 | 4 |
| 2 | 3.0 | 4 |
| 15 | 2.0 | 3 |
| 2 | 3.0 | 4 |
| 2 | 3.0 | 3 |
| 1 | 3.0 | 3 |
| 32 | 2.0 | 2 |
| 19 | 1.0 | 1 |
| 1 | 2.0 | 2 |
| 16 | 0.3 | 0 |
| 19 | 1.0 | 2 |
| 15 | 2.0 | 2 |
| 30 | 3.0 | 3 |
| 18 | 3.0 | 2 |
| 19 | 3.0 | 3 |
| 19 | 1.0 | 1 |
| 31 | 3.0 | 4 |
| 15 | 1.3 | 1 |
| 32 | 0.8 | 1 |
| 1 | 1.3 | 1 |
| 16 | 1.7 | 1 |
| 30 | 0.9 | 1 |
| 1 | 1.5 | 1 |
| 31 | 2.7 | 2 |
| 19 | 1.9 | 2 |
| Number of teeth 26 | Mean = 2.16 ± 0.55 | Mean = 2.11 ± 0.67 |

Circuit Description

In a similar examination of non-carious teeth (see Example 2 below), electrical conductance readings showed a mean value of 0.0 μA and mean demineralization scores were zero.

Figure 5:
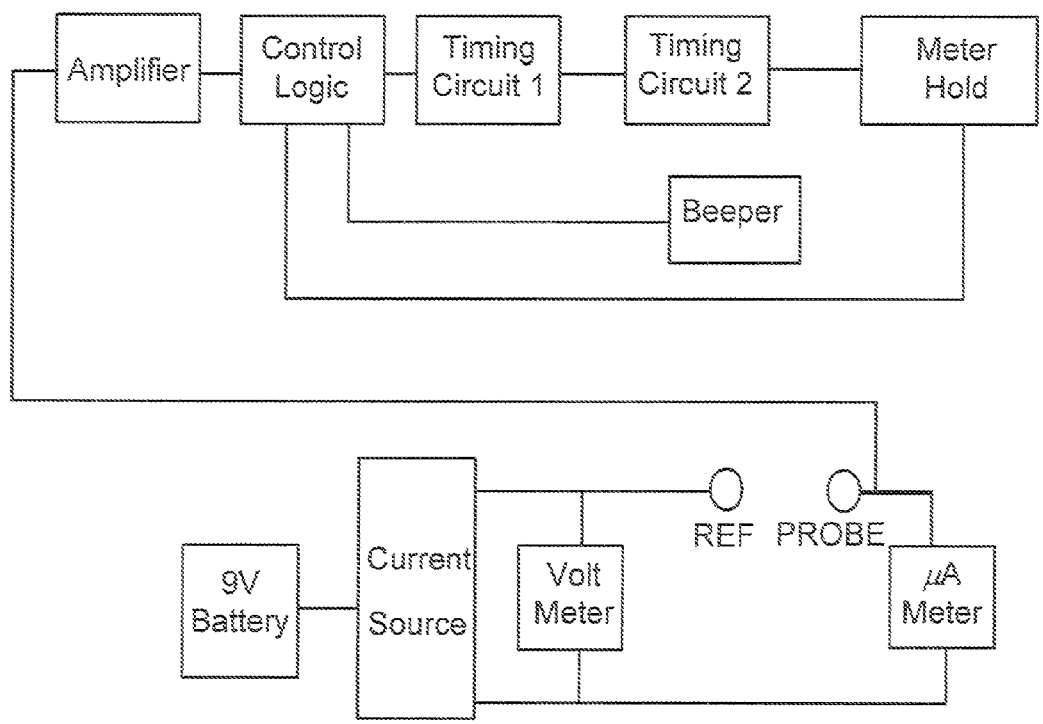
FIG. 5 is a schematic representation of the components of an embodiment of the present invention.

As seen in FIG. 5, during caries probing, the present device is essentially an open circuit instrument. The circuit is closed when there is fluid traversing the lesion site and the fluid makes contact with a measuring electrode with or without a conducting aid such as a paste or saliva. The circuit may include a pathway of current flow from a patient's forearm, back of neck or cheek through his or her body to the patient's tooth being measured. This circuit completion may be achieved via the indicator and reference electrodes with a µA meter and/or voltmeter measuring unit in between. A suitable reference is an EKG type of silver/silver chloride electrode (Silver Mae Trade plus Tab, Cardiology Shop, Berlin, Mass. 0150) attached to the ventral surface of the forearm. A lip hook can also be used but is not desirable because it hinders application of the measuring electrode by the dentist or other healthcare worker.

As can be appreciated from FIG. 5, the present device may be powered by two batteries. The first battery powers a µA meter and if included, a voltmeter. The current source output voltage is unregulated (9 volts down to 1 volt) and the current output as indicated above is limited to 10 µA. A second battery may power the current source circuitry and the control and monitoring circuits (see above). This battery may have a voltage in the range 6.3 to 9.0 volts. At a voltage below 6.3 volts, the battery should be replaced. In some embodiments, determination of battery life may include turning on a battery test switch. The first battery may be similarly replaced when the meter displays a low battery condition.

A small load indicates the presence of a cavity at an early stage of development; it is associated with a high resistance (e.g. 22 megohms). The lesion being evaluated in such a situation will draw a small amount of current and show a small decrease in the voltage. Should the load be higher, (e.g. one reflected by a resistance between 100,000 and 600,000 ohms), the current flow will be greater; decrease in voltage will become larger and a more advanced cavity is indicated. Should the load be still higher, resistance will be very low (e.g. between 1,000 and 100,000 ohms). The current will rise and reach close to the maximum current of 10 µA; correspondingly, the voltage will drop to 1 volt and a more advanced cavity would be indicated.

Additional components in the completed meter circuit may include a resistor (R1), a resistance shunt (Rs) and the µA meter. R1 is calculated by the formula R1=V/A where V is voltage and A is current in amperes. Design is such that the current source output voltage will drop no lower than 1 volt. This occurs when the reference electrode and the dental probe are intentionally shorted (no patient in the circuit) as is done as a systems test, when carrying out pre-testing as described below. The maximum current source output in this situation is 10 µA and R1=1 volt/10 microamps=100,000 ohms (see Tables 1 and 2).

The Rs shunt may be set to 1,000 ohms for a 200 µA digital panel meter with a 200 mv range (full scale). In that case, Rs=Vm/Im=200 mv/200 µA=1,000 ohms. The completed circuit meter readings in the instant device for various resistance values placed between the reference electrode and the instant device probe, simulates dental caries conditions and the results are shown in Tables 1 and 2. The calculated resistance values will include the circuit resistors, R1+Rs, as stated above; these values are shown in the R=V/I column in Tables 1 and 2.

The voltage and current measurements with the present device (Tables 1 and 2) both show a pattern that is directly related to dental caries presence. The magnitude of the cavity is related to the magnitude of the current, the voltage decrease and the combination of both the voltage and current changes. The battery voltage range differences are in Table 1 (8.61V) and Table 2 (6.37V); they yield an insignificant difference in circuit resistance plus a micro-ampere difference ranging from 0 at 80K ohms to a maximum of 1.61 µA at 1 megohm.

The values for R=V/I, calculated using Ohm's Law, are shown in Tables 1 and 2. The calculated values for circuit resistance closely match the Ohms column and the R=V/I calculated resistance column; this includes $R_1$ (100K)+Rs (1K) for both battery voltage levels.

Voltage Regulation

The present device may use a 9 volt unregulated, 10 µA current limited power supply. The use of an unregulated supply allows the voltage to drop (e.g. 9 volts to 1 volt) as the load is increased. If desired, this allows voltage data to be recorded in addition to current data.

A constant voltage regulated supply limited to 10 µA output may also be used. The difference is that, as the load is increased, the voltage holds constant at 9 volts and the current still rises (e.g. 0 to 10 µA). The current data available are recordable and values are directly related to the magnitude of the caries lesions.

In essence, the important aspect of the instant device is the development of (i) a specialized measuring probe, (ii) a method of measuring electrical conductance that includes use of the conductivity of a patient's body and the supplying of a current source limited to 10 µA of current and (iii) a method of being able to rapidly probe for active sites and record conductance rapidly and accurately. As indicated above, measurement is one that either involves no conduction (i.e. open circuit) when there is no caries, or one that does involve conduction (i.e. closed circuit) when there is caries present.

Processor and Storage

In some embodiments, the probe is coupled to a processor and a storage medium. Any suitable processor can be used, including a combination of individual processors. Any suitable storage medium can be used. Storage media may include volatile, nonvolatile, removable, and non-removable media implemented in any method or technology for storage of information, such as computer readable instructions, data structures, program modules, or other data. Examples of storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device or other processor. Methods of communication between components of the arrangements described herein can include both wired and wireless (e.g. acoustic radio-frequency, optical, or infrared) communications methods. By way of example, wired communications can use items such as twisted pair, coaxial cable, fiber optics, wave guides, and other wired media and wireless communications can use methods such as those above.

In at least some embodiments, the processor is coupled to a storage medium and sends data to the storage medium for storage or further calculations. In some embodiments, the storage medium may be portable, such as a compact disk. The storage medium may automatically record or log data sent to it by the processor. In some embodiments, the storage medium stores patient data in a log including, for example, patient name, date of visit, number of caries detected and/or location of caries.

The processor may also be coupled to an indicator. The indicator may be configured on either a probe or as part of the processor. In at least some embodiments, when a caries lesion is detected, one or more signals may be emitted. In another embodiment, a signal may be emitted when electrical conductivity is first detected. Many different types of signals may be emitted from the indicator including, for example, at least one auditory signal, at least one visual signal, at least one tactile signal, at least one olfactory signal, a telemetry signal to another device, or the like or combinations thereof. For example, an emitted signal may include one or more beeps, chirps, squeaks, chimes, rings, the activation or de-activation of one or more lights or light-emitting diodes one or more times, a message may be displayed on one or more displays, one or more vibrations or tactile pulses, the emission of one or more peculiar odors, and the like or combinations thereof. The indicator may be activated for any set period of time. In some embodiments, the indicator is activated for at least a period of 3 to 5 seconds, so that the dentist or dental care provider such as a hygienist can verify or record the presence of the caries.

As discussed, the processor may be coupled to an indicator in the form of a message or emitted signal. Alternatively, the indicator may be in the form of a graphical representation of the teeth. As the probe is moved over the teeth, the area may be mapped onto a graphical representation, showing possible caries. Such a graphical representation may be helpful in identifying possible problematic areas for the attending dentist or dental care provider.

Device Operation.

Figure 6:
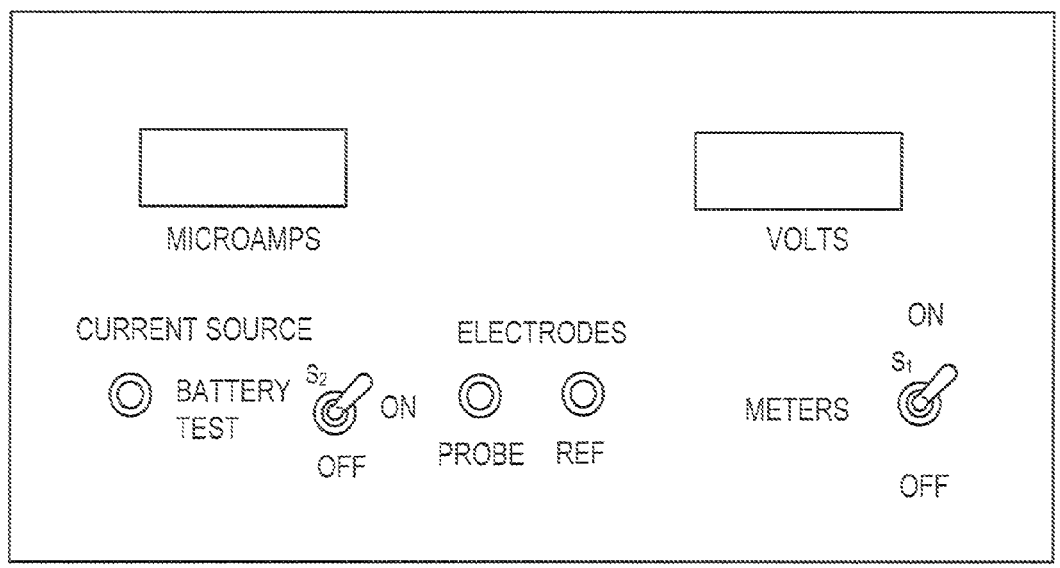
FIG. 6 is a schematic front view of the front panel of an embodiment of the present invention.

FIG. 6 is a schematic front view of the front end of a caries measuring instrument. Operation of the device may be as follows: (i) The instrument is turned on by moving switch S1 to the ON position; the μA meter will read 0.00. If a low battery condition is displayed, the meter battery needs to be replaced; (ii) Switch S2 is moved to the BATTERY TEST position; the current source battery needs to be replaced if the test light does not illuminate; (iii) Switch S2 is moved to the ON position and (iv) the probe and reference electrode, which are connected to the device by jacks, are used to test whether the circuits are functioning properly. The output of the current source supplies 9 volts at 0 μA in the open circuit state and a maximum of 1 volt and 10 μA in the shorted closed circuit condition, i.e. when reference and probe electrodes are in contact with each other.

To carry out the testing, readings may be made by first having the system in its open position and to then test if reading range is at its maximum. For the latter, the probe tip is placed in contact with the reference electrode so that the circuit is shorted. This activates an auditory component (a beeper) in the measuring unit for a period of time that indicates to the operator that he or she has made electrical contact. In some embodiments, the auditory component is activated for 1, 2, 3, 4, 5 or 10 seconds. When the beeping of the auditory component stops, the electrode is removed from contact with the measuring site. At the end of the beep, a five second numerical hold circuit is triggered which results in the display of no more than 10 μA on the μA meter and no less than 1 volt on the voltmeter. The reading may hold for five seconds to allow time for reading recording; the meters then return to zero μA and full battery voltage. The system is now ready for successive intermittent probing for hidden dental caries lesions with the indicator electrode. Sliding probing can also be done where the probe is run along fissures and a beep or beeping will locate early hidden caries lesions. An immediate intermittent probe thereafter will confirm lesion presence and its magnitude.

To enable device portability, batteries may be used. This eliminates the need for patient isolation techniques, power cords and reduces cost. A line powered or battery eliminator can also be constructed. The use of line power or a battery eliminator transformer requires a power cord and the addition of patient isolation techniques. The voltages supplied to and by the circuitry in the meter are set and will not vary like a battery can, as it gradually discharges during use. Circuit operation of the current source is the same.

These features will allow the same data from all such meters. If eliminating the need to manually record data is desired, a method may be introduced to record the data in a memory or print the data instead.

The details of the device are provided in the Examples given below which are provided as an illustration of the invention only and therefore should not be construed to limit the scope of the present invention.

Example 1

An apparatus was assembled to simulate the in vivo condition to show that fluid can move coronally through the apical foramen of a tooth (from underlying tissue fluid) and then through the pulp and thereafter through the dentine to fill any breached or partly breached (porous) enamel spaces. In doing so, the nature of the electrical conductance circuit involved is demonstrated along with its open and closed nature during measurements.

The apparatus is also of considerable use for the testing beforehand of probe tips for their suitability for use in the measuring instrument. It is also of use for training health care providers before proceeding to work on patients.

The device consists of a Petri dish (9 cm diameter) without its lid, covered with a rubber or cardboard sheet (15 cm square×2 mm thick) with a hole in the center for a tooth to be placed in an upright position ready for probing and electrical testing (cf. rubber dam used in vivo). Another hole in the sheet is used to accommodate a reference electrode as above. Still another hole is cut to enable addition or removal of saliva, serum or other fluids, as desired or appropriate.

The sheet is supported by a 15 cm×7 mm thick wooden frame placed over the Petri dish. Thirty ml of 0.9% (w/v) NaCl solution (i.e. saline) is added to the Petri dish and the roots of each tooth undergoing measurement is pressed through the hole in the center of the rubber sheet until the apical portion of the root is immersed about 2 to 3 mm into the saline in the Petri dish. The saline enters the pulp chamber through the root canal or canals of the tooth being tested. It then passes from the pulp and through the dentinal tubules to reach the pits, fissures or fossae under test. If any covering enamel is not intact (i.e. porous or breached), then current will be detected and measured.

The reference electrode utilized in making conductance determinations consists of a convenient length of platinum wire placed into the saline solution in the Petri dish and is connected to an insulated wire leading to the measuring instrument. The indicator electrode and its replaceable measuring tips may be similar to those described above with reference to FIGS. 3 and 4.

Example 2

In a set of experiments to compare sound and carious teeth and confirm such to be the case by biopsy, electrical current at 6 to 8 occlusal surface sites per tooth were measured in 26 non-cavitated carious and in 13 freshly erupted (and hence, clearly non-cavitated and non-carious) teeth. At each site, readings were made in triplicate. Each time beforehand, the tooth was dried by air-blowing for 5 to 10 seconds prior to the taking of measurements. The crown of each tooth was then sectioned transversely with tooth slices cut progressively from the occlusal to the cemento-enamel junction area. This gave slices that were each 630 μm thick. In a re-constructed sectioned tooth, slices would be spaced 150 μm apart due to the thickness of the diamond blade in a low speed saw (Isomet 11-1180, Buehlar, Evanston, Ill.) used for the slicing. Each horizontal section was photographed in color and examined visually for demineralization, which indicated extent of lesion progression and was scored on a scale of 0-4.

Electrical conductance ranged between 0.3 and 3 μA in the occlusal sites in the 26 carious teeth measured as seen in Table 3 and was zero in all of the occlusal sites measured in the 13 non-carious controls as seen in Table 4. The teeth identified in Tables 3 and 4 are numbered in accordance with the Universal System of Tooth Numbering. The right maxillary third molar is designated "1" and the count increases to the left. The left mandibular third molar is designated "17" and the count increases to the right along the bottom teeth.

TABLE 4

Electrical current and Demineralization Scores of Control Teeth

| Tooth # | Current (μA) | Demineralization score |
|---|---|---|
| 1 | 0.0 | 0 |
| 15 | 0.0 | 0 |
| 32 | 0.0 | 0 |
| 32 | 0.0 | 0 |
| 32 | 0.0 | 0 |
| 17 | 0.0 | 0 |
| 16 | 0.0 | 0 |
| 19 | 0.0 | 0 |
| 16 | 0.0 | 0 |
| 3 | 0.0 | 0 |
| 32 | 0.0 | 0 |
| 16 | 0.0 | 0 |
| 31 | 0.0 | 0 |
| Number of teeth 13 | Mean = 0.0 | Mean = 0 |

Visual examination of the horizontal sections of the carious group of teeth showed a mean demineralization score of 2.11±0.67 (S.D.) (see Table 3 above) on a 0-4 scale as described below in Table 5. Their mean electrical conductance value (see Table 3) was 2.16±0.55 (S.D.) μA. In contrast, the control group of teeth showed a mean electrical conductance of 0.0 μA (Table 4) and no mineral loss was visible in these sections. Their mean demineralization score was 0. The difference in the electrical current values between the two groups was highly significant by the Student t test as was the difference in their demineralization values ($p<0.001$).

Example 3

Figure 7:
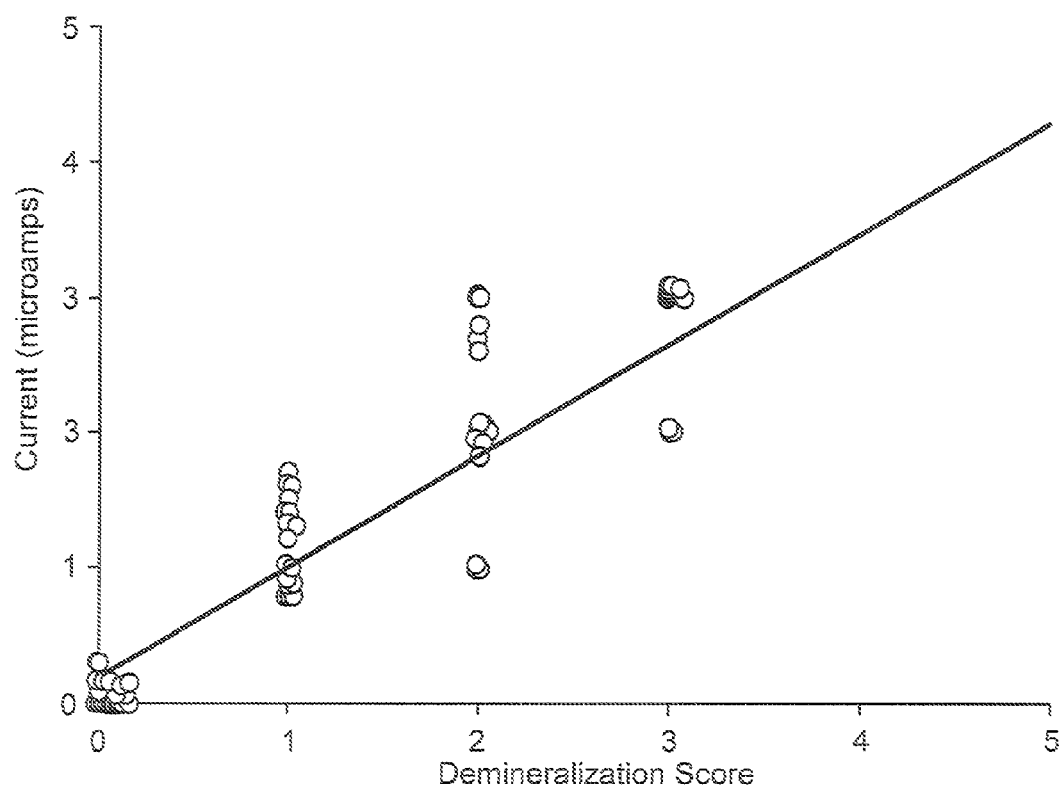
FIG. 7 is a graph showing the relationship between electrical conductance and demineralization.

The occlusal surfaces of forty extracted permanent molars were each first measured with the measuring device to detect presence of caries lesions and to then confirm their presence by tooth biopsy as in Example 2 above. This group of teeth showed electrical current values between 0 and 4 μA. Occlusal sites were selected in each slice and electrical conductance was measured in each location in triplicate. The teeth were then biopsied by sectioning as in Example 2 and visually examined and scored for demineralization from color photographs thereof. Electrical current was plotted against demineralization scores (FIG. 7). Correlation between electrical conductance and detection by biopsy was very high ($r=0.914$; $p<0.001$).

Example 4

Batteries lose voltage with use. Such discharge may affect the stability of instrument readings. To test for this possibility, a 100K resistor was introduced into the instant device between the probes of the measurement instrument. This adds to R1 and Rs a value of 101,000 ohms. In Table 1, with a battery voltage of 8.61 volts, the instrument reads 1.98 volts and 9.82 μA. Using Ohms Law, R=V/I, this works out to 201,000 ohms. Table 2 shows similar measurements when the battery voltage is 6.37 volts. Connecting the same 100K resistor between the probes of the present device results in meter readings of 1.98 volts and 9.83 μA. This also calculates out to 201,000 ohms.

In comparing Tables 1 and 2, the differences in the calculated values of column R=V/I are insignificant. A review of the μA column shows a difference of 0 μA at 80,000 ohms, and a maximum difference of 1.6 μA at 1,000,000 ohms. This difference in μA may be insignificant in determining the magnitude of caries lesions. Thus, the accuracy of the measuring device in detecting dental caries has been demonstrated. Thus, readings are not affected as the 9 volt battery power source loses some of its charge.

Example 5

A 14-month study was carried out to compare detection in vivo of occlusal caries lesions in the occlusal surfaces of the first permanent molars of Venezuelan children by electrical conductance and by visual-tactile means. Two hundred children, 9 to 11 years of age, from Unidad Educativa Baute in Venezuela participated in this investigation. Of the 200 children accepted, 119 remained at the end of this investigation and these are the basis of the data analysis. The visual-tactile and electrical conductance methods were both used to detect carious lesions at baseline and after 14 months. The occlusal surface examinations were done by two examiners. One performed the visual-tactile examination using artificial light, probe and dental mirror; the other utilized the caries detection device of the present invention. Both examiners were standardized beforehand for their respective methods. Visual-tactile examination used a DMFS scoring procedure based on the criteria shown in Table 5:

TABLE 5

The recording criteria used in the visuo-tactile examination method.

| | |
|---|---|
| 1a: | Change in enamel surface translucency or opacity that is distinctly visible after air drying |
| 1b: | Opacity distinctly visible while surface is still wet. |
| 1c: | Localized enamel breakdown where the enamel is opaque or discolored. |
| 1d: | Cavitated enamel |
| 2: | Filled tooth surface |
| 3: | Extracted tooth surface |
| 4: | No or slight change in enamel translucency (sound) |
| 5: | Unerupted surface |

DMFS scoring:
1a, b or c is scored D ½;
1d is scored D1;
2 is scored Filled;
3 is scored Missing; and
4 is scored Sound.

For this example, surfaces were scored carious if any of criteria 1a to 1d were met and sound if criterium 4 was met. The results of such carious/sound scoring are shown in Tables 6 and 7, below:

TABLE 6

Number and percentage of occlusal surfaces in first permanent
molar teeth at baseline showing status according to the (i) Electrical
Conductance and (ii) Visual-Tactile methods utilized.

| First Molar Teeth (6) in | Detection methods | | | |
|---|---|---|---|---|
| | Electrical Conductance (number) | | Visual-Tactile (number) | |
| Quadrants 1-4 | Sound | Carious | Sound | Carious |
| 16 | 7 (5.9) | 112 (94.1) | 81 (68.1) | 38 (31.9) |
| 26 | 21 (17.6) | 98 (82.4) | 80 (67.2) | 39 (32.8) |
| 36 | 26 (21.8) | 93 (78.2) | 45 (37.8) | 74 (62.2) |
| 46 | 24 (20.2) | 95 (79.8) | 52 (43.7) | 67 (56.3) |
| Total | 78 (16.4) | 398 (83.6) | 258 (54.2) | 218 (45.8) |
| Carious/sound ratio | 5.10 | | 0.84 | |

Values in parentheses are expressed in percentages.

TABLE 7

Number and percentage of occlusal surfaces in first permanent
molar teeth at 14 months showing status according to the (i) Electrical
Conductance and (ii) Visual-Tactile methods utilized.

| First Molar Teeth (6) in | Detection methods | | | |
|---|---|---|---|---|
| | Electrical Conductance (number) | | Visual-Tactile (number) | |
| Quadrants 1-4 | Sound | Carious | Sound | Carious |
| 16 | 4 (3.4) | 115 (96.6) | 68 (57.2) | 51 (42.8) |
| 26 | 4 (3.4) | 115 (96.6) | 63 (53.0) | 56 (47.0) |
| 36 | 9 (7.6) | 110 (92.4) | 33 (27.7) | 86 (72.3) |
| 46 | 9 (7.6) | 110 (92.4) | 24 (20.2) | 95 (79.8) |
| Total | 26 (5.5) | 450 (94.5) | 188 (39.5) | 288 (60.5) |
| Carious/sound ratio | 17.30 | | 1.53 | |

Values in parentheses are expressed in percentages.

Figure 11:
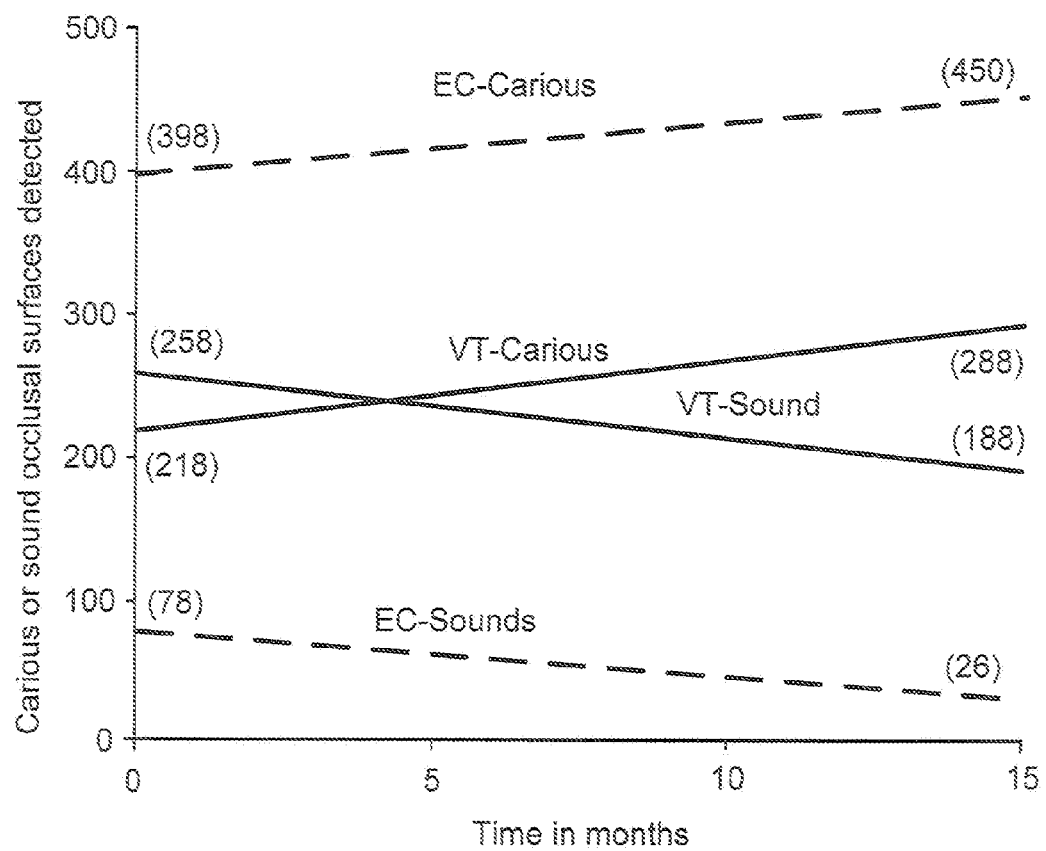
FIG. 11 is a graph comparing detection of carious and sound tooth surfaces at baseline and after 14 months by visual-tactile (VT) and electrical conductance (EC) means as per Tables 6 and 7.

At baseline, the electrical conductance (EC) method detected many more occlusal surfaces with caries lesions than was observed with the visual-tactile procedure (see Table 6 and particularly the carious/sound ratios shown therein; i.e. 5.10 by EC and 0.84 by visual-tactile). This wide difference can be attributed to the wide difference in their detection capabilities, namely that EC examination is capable of detecting lesions at a much earlier stage in their development than can be detected by visual-tactile means, when many very early lesions are not yet visible by visual-tactile examination. A second examination was done 14 months after baseline to enable lesions to develop and thus become more readily detectable by both methods. The results showed that caries increased between baseline and 14 months by both methods (Tables 6 and 7 and see FIG. 11). From Tables 6 and 7, one can see that with time (i.e. after 14 months) the higher ratio of carious to sound surfaces is sustained as caries progresses with age (i.e. 17.30 by EC and 1.53 by visual-tactile). FIG. 11 clearly shows the much greater caries detection capability with EC measurement than with the classical mirror and probe method, which is what should be expected because of the much greater and earlier detection capability by EC measured with the device of the present invention.

Earlier detection by electrical conductance is particularly valuable at the pre-cavity stage of caries development, because there are major treatment consequences of early detection. Most significant is that treatment can be achieved by simpler means, namely re-mineralization procedures, whereas later detection by visual-tactile means involves larger lesions (cavities) and use of so-called drilling and filling restorative procedures.

Example 6

The size and shape of the removable measuring tips of the device of the present invention are important features. The probe tips are able to fit into caries-prone sites more readily than heretofore. Probe tips ranging in tip sizes were tested and compared to the probing ends of a range of explorer probes normally used in conjunction with hand mirrors to probe for and locate presence of early cavities.

Figure 8:
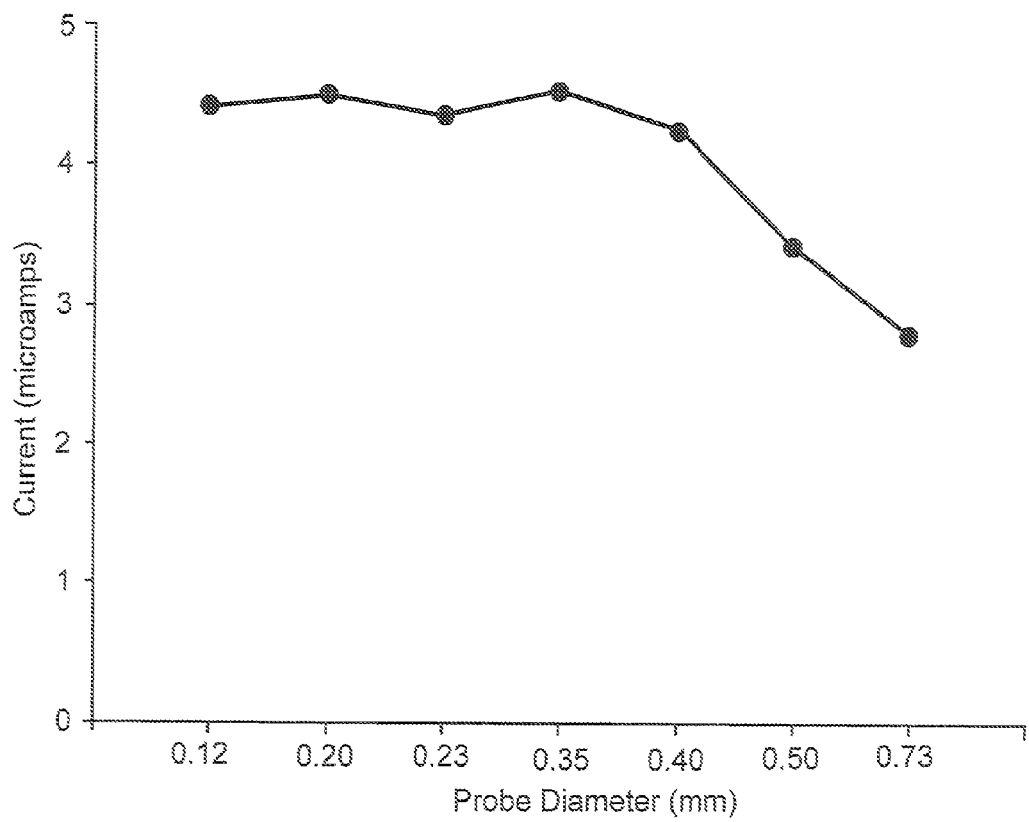
FIG. 8 is a graph showing the relationship between electrical conductance and probe tips of different tip diameters in a molar tooth fissure site.

Probing tips ranging from 0.12 to 0.73 mm in diameter at their actual tips were examined for their ability to measure electrical conductance in molar teeth using the apparatus described in Example 1. Results are presented in FIG. 8. Tips with a diameter ranging from 0.12 to 0.40 mm gave similar results. For tips with diameters greater than 0.40 mm, electrical conductance values, measured in μA, dropped as would be expected because the tip would not be able to penetrate and fit sufficiently into a pit, fissure or fossa site.

Figure 9:
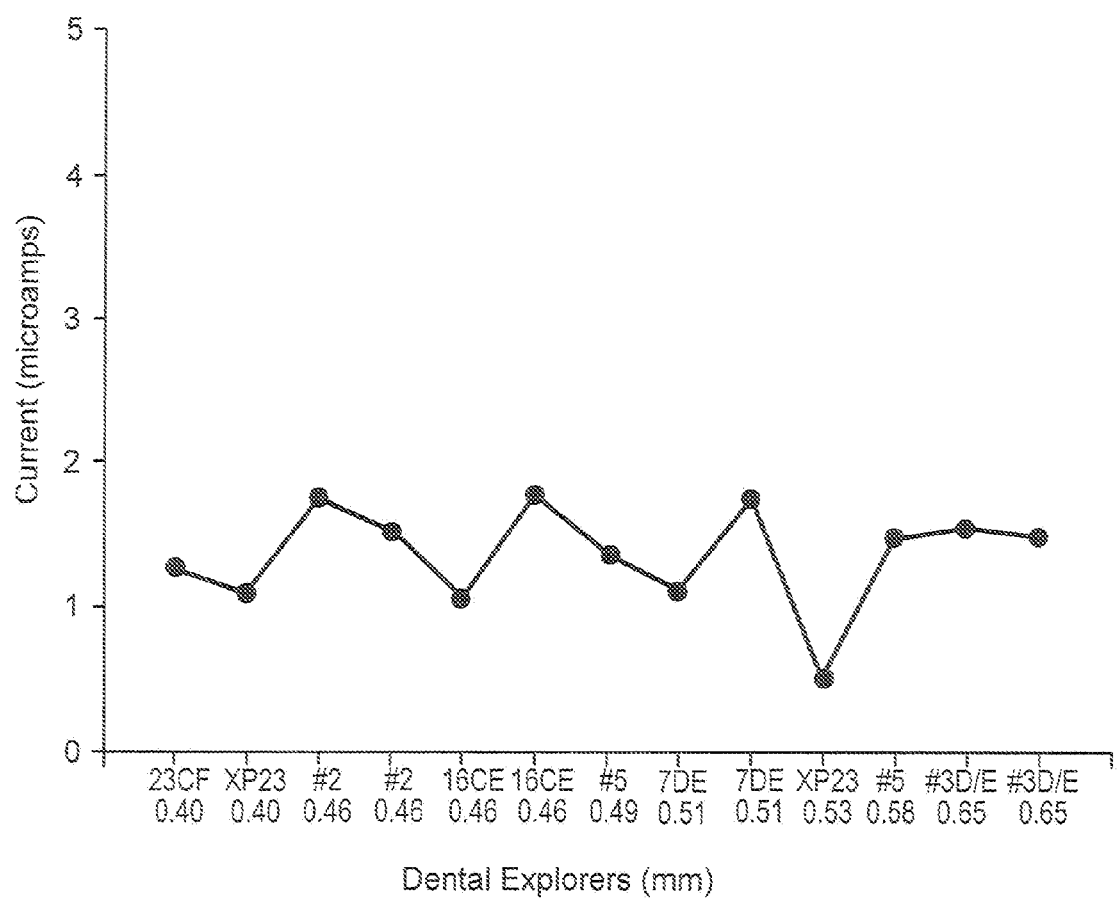
FIG. 9 is a graph showing the relationship between electrical conductance and commercially available explorer tip diameters in a molar tooth fissure site.
Figure 10:
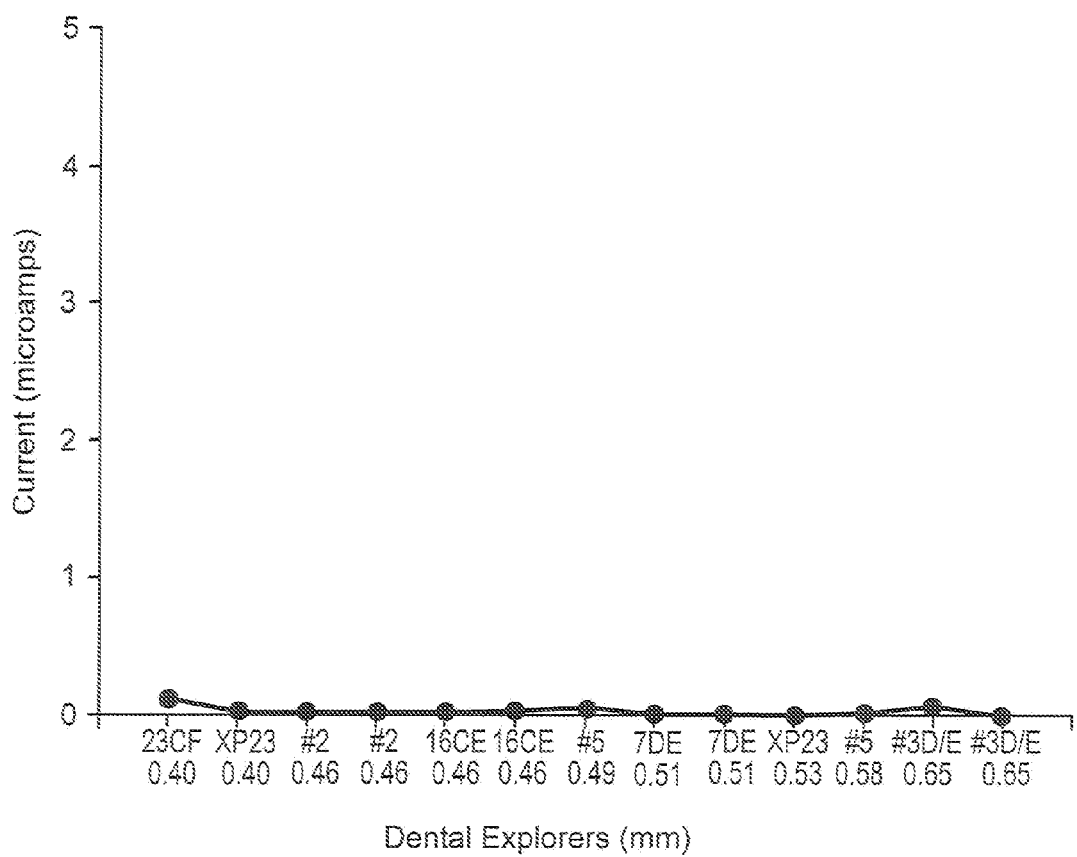
FIG. 10 is a graph showing the relationship between electrical conductance and the diameter of different commercially available dental explorers in another (less accessible than in FIG. 10) molar tooth fissure site.

Similar electrical conductance measurements were also made for a range of commercially available dental explorers coupled to the device of Example 1 (FIGS. 9 and 10). Their tip diameters were larger in size than the described tip diameters proposed herein and hence caries-prone site penetration can be expected to be less, as in FIG. 9 and even less as in FIG. 10, These explorers are available commercially and comprise a representative sample. Their tips are larger and slightly more rounded at their tips than are the tips of the present invention. Accordingly, the tips of the present invention were more suitably shaped and finer than the commercial explorer tips and thus could penetrate into occlusal sites more readily. The results in FIG. 10 showed virtually no electrical conductance which is consistent with penetration of the probes being insufficient to give much current flow. FIG. 9 indicates some penetration. Thus, the size of the prior art tips limited their ability to penetrate sufficiently into caries prone sites and hence meant unsatisfactory and less sensitive diagnostic capability. This limitation also applies to tufted tips (i.e. bundle of tufts) presently available. Such tufts cannot penetrate fissures deeply and their behaviour is like that of the oversized electrodes in FIGS. 8, 9 and 10. Also such a tufted electrode tip lacks the rigidity that enables reproducible probe placement into a fissure site.

What is claimed is:

1. A device for detecting non-cavitated dental caries lesions in a human patient, in the absence of visible enamel breaching or visible enamel mineral loss, comprising: a measuring electrode having an electrically conductive tip, said tip being dimensionally configured to fit within and contact the bottom of a dental fissure and provide electrical contact only with any dentinal fluid at the bottom of the fissure, and said conductive tip comprising a shaft and a taper portion at an angle with the shaft, the taper portion having a progressively reduced diameter tip portion to provide a pointed tip for penetration into a fissure and contact with any dentinal fluid at the bottom of the fissure; a reference electrode, the reference electrode being configured for electrical contact with the patient's body; and measuring means for determining electrical resistance between the measuring electrode and the reference electrode thereby detecting non-cavitated dental caries lesions in the absence of visible enamel breaching or visible enamel mineral loss, wherein the device is further configured to receive a current source for providing electrical current between the measuring electrode and the reference electrode and wherein the device detects a non-cavitated dental caries lesion when an electrical resistance of between 600,000 and 22,000,000 ohms is measured.

2. The device of claim 1, further comprising means for regulating said electrical current not to exceed 10 µA.

3. The device of claim 1, further comprising an indicator configured to signal electrical contact of the measuring electrode with dentinal fluid.

4. The device of claim 3, wherein said signal is auditory.

5. The device of claim 1, further comprising a first timing circuit configured to display said measured electrical resistance for a predetermined amount of time.

6. The device of claim 5, further comprising a second timing circuit, configured to register said measured electrical resistance after a predetermined period of continuous contact between the measuring electrode and dentinal fluid.

7. The device of claim 1, wherein the measuring electrode includes an electrically insulated handle and an electrically conductive tip.

8. The device of claim 1, wherein the shaft of said electrically conductive tip of the measuring electrode has a length of 20 to 40 mm and a diameter of 1.0 to 2.0 mm and said taper portion has a length of 6.0 to 9.0 mm.

9. The device of claim 8, wherein the shaft and the taper portion are at a 90° angle to each other.

10. The device of claim 8, wherein the taper portion has a diameter of 0.2 to 0.4 mm and the tip portion tapers to a point over a length of 1.6 to 2.0 mm.

11. The device of claim 7, wherein the conductive tip comprises stainless steel.

12. The device of claim 1, wherein the reference electrode is configured for electrically conductive contact with a body surface.

13. The device of claim 3, wherein the indicator is configured to signal electrical contact at predetermined intervals.

14. The device of claim 1, further comprising a storage medium capable of receiving and storing electrical resistance data from said measuring means.

15. The device of claim 1 wherein the electrically conductive tip is attached to a measuring probe by a knurl-type locking means that enables adjustment of a protrusion of the electrically conductive tip from the measuring probe.

16. The device of claim 1 wherein the electrically conductive tip is attached to a measuring probe by a contact spring to provide electrical communication between the electrically conductive tip and the measuring probe.

17. The device of claim 16 wherein the electrical conductive tip is co-axially stiffened.

18. The device of claim 1, wherein the pointed tip has a diameter of between 0.03 and 0.06 mm.

19. The device of claim 18, wherein said pointed tip has a diameter of between 0.04 and 0.06 mm.

20. The device of claim 19, wherein said pointed tip has a diameter of between 0.03 and 0.05 mm.

21. The device of claim 2, wherein the current source is a 9 volt battery.

22. The device of claim 21, further comprising means for regulating the current not to exceed 10 µA.

23. A method for detecting non-cavitated dental caries lesions in the absence of visible enamel breaching or visible enamel mineral loss in a human patient, the method comprising the steps of: providing a reference electrode of a device for electrically conductive contact with a patient's body and providing a measuring electrode having an electrically conductive tip, said tip being dimensionally configured to fit within and contact the bottom of a dental fissure and provide electrical contact only with any dentinal fluid at the bottom of the fissure, and said tip comprising a shaft and a taper portion at an angle with the shaft, the taper portion having a progressively reduced diameter tip portion to provide a pointed tip for penetration into a fissure and contact any dentinal fluid at the bottom of the fissure; contacting the tip of the measuring electrode within and at the bottom of a dental fissure; providing electrical current by said device between the measuring electrode and the reference electrode; and determining electrical resistance by said device between the measuring electrode and the reference electrode and thereby detecting a non-cavitated dental caries lesion when said electrical resistance is between 600,000 and 22,000,000 ohms.

24. The method of claim 23, further comprising means for regulating the electrical current not to exceed 10 µA.

25. The method of claim 23, further comprising the step of signaling electrical contact of the measuring electrode with the dentinal fluid.

26. The method of claim 23, wherein the electrically conductive tip provides electrical contact with dentinal fluid present within said fissure after surface air drying of said patient's tooth and in the absence of introduction of a conducting fluid to said patient's tooth.

27. The method of claim 23, wherein the pointed tip has a diameter of between 0.03 and 0.06 mm.

28. The method of claim 27, wherein said pointed tip has a diameter of between 0.04 and 0.06 mm.

29. The method of claim 28, wherein said pointed tip has a diameter of between 0.03 and 0.05 mm.

* * * * *